United States Patent
Funkner et al.

(10) Patent No.: US 11,279,923 B2
(45) Date of Patent: Mar. 22, 2022

(54) METHOD FOR PURIFYING RNA

(71) Applicant: CureVac AG, Tübingen (DE)

(72) Inventors: Andreas Funkner, Tübingen (DE);
Stefanie Sewing, Tübingen (DE);
Isabel Strobel, Tübingen (DE);
Thorsten Mutzke, Tubingen (DE)

(73) Assignee: CureVac AG, Tübingen (DE)

( * ) Notice: Subject to any disclaimer, the term of this patent is extended or adjusted under 35 U.S.C. 154(b) by 0 days.

(21) Appl. No.: 16/464,152

(22) PCT Filed: Nov. 28, 2017

(86) PCT No.: PCT/EP2017/080703
§ 371 (c)(1),
(2) Date: May 24, 2019

(87) PCT Pub. No.: WO2018/096179
PCT Pub. Date: May 31, 2018

(65) Prior Publication Data
US 2020/0318097 A1    Oct. 8, 2020

(30) Foreign Application Priority Data

Nov. 28, 2016  (WO) ................ PCT/EP2016/079026

(51) Int. Cl.
*C12N 15/10*    (2006.01)
(52) U.S. Cl.
CPC ....... *C12N 15/1006* (2013.01); *C12N 15/101* (2013.01)
(58) Field of Classification Search
CPC .................. C12N 15/1006; C12N 15/101
USPC ...................................... 536/127
See application file for complete search history.

(56) References Cited

U.S. PATENT DOCUMENTS

| | | |
|---|---|---|
| 2005/0032730 A1 | 2/2005 | von der Mülbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr et al. |
| 2008/0267873 A1 | 10/2008 | Hoerr et al. |
| 2009/0048437 A1 | 2/2009 | Myo-Yong et al. |
| 2009/0048439 A1* | 2/2009 | Weisburg ............ C12N 15/1006 536/25.41 |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | von der Mülbe |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |

(Continued)

FOREIGN PATENT DOCUMENTS

| | | |
|---|---|---|
| WO | WO 2008/077592 | 7/2008 |
| WO | WO 2014/152031 | 9/2014 |
| WO | WO 2017/021546 | 2/2017 |
| WO | WO 2017/137095 | 8/2017 |
| WO | WO 2017/140905 | 8/2017 |

(Continued)

OTHER PUBLICATIONS

MAXIscript® Kit protocol. 2008 Ambion, Inc., Revision Date: Jul. 22, 2008. (Year: 2008).*

Balasubramanian et al. Enhanced detection of pathogenic enteric viruses in coastal marine environment by concentration using methacrylate monolithic chromatographic supports paired with quantitative PCR. Water Research 106 (2016) 405-414 (Available online Oct. 8, 2016). (Year: 2016).*

(Continued)

*Primary Examiner* — Yih-Horng Shiao
(74) *Attorney, Agent, or Firm* — Parker Highlander PLLC

(57) ABSTRACT

The present invention relates to methods for purifying RNA by chromatography under high salt conditions, e.g. by hydrophobic interaction chromatography.

21 Claims, 4 Drawing Sheets

Figure 1:
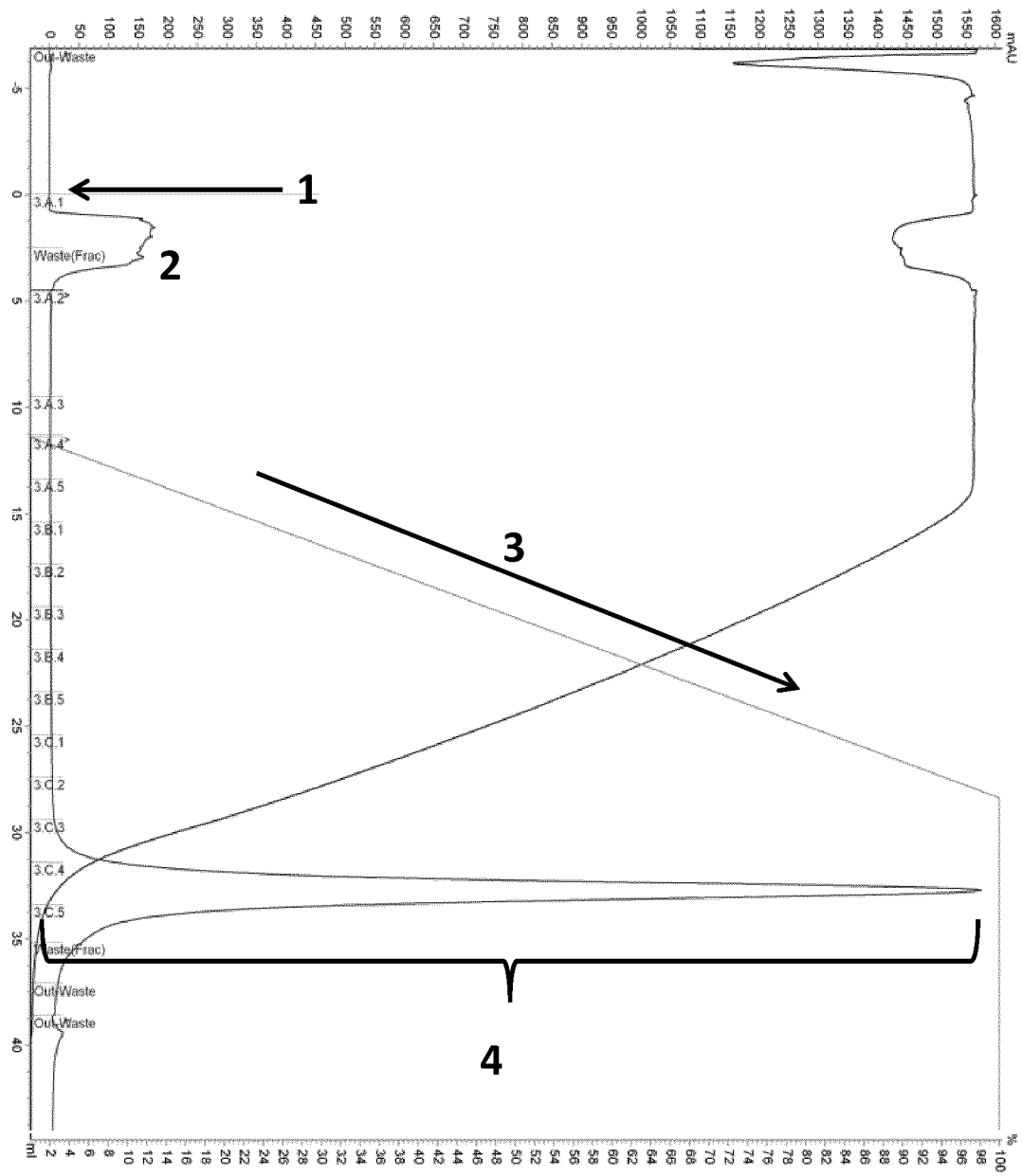

Specification includes a Sequence Listing.

(56) References Cited

U.S. PATENT DOCUMENTS

| | | |
|---|---|---|
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |
| 2019/0160164 A1 | 5/2019 | Rauch et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0241633 A1 | 8/2019 | Fotin-Mleczek et al. |
| 2019/0249219 A1 | 8/2019 | Reichert et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1 | 11/2019 | Fotin-Mleczek et al. |
| 2019/0351044 A1 | 11/2019 | Jasny et al. |
| 2019/0351047 A1 | 11/2019 | Jasny et al. |
| 2019/0351048 A1 | 11/2019 | Rauch |

FOREIGN PATENT DOCUMENTS

| | | |
|---|---|---|
| WO | WO 2017/186928 | 11/2017 |
| WO | WO 2017/191258 | 11/2017 |
| WO | WO 2017/212008 | 12/2017 |
| WO | WO 2017/212009 | 12/2017 |
| WO | WO 2018/078053 | 5/2018 |
| WO | WO 2018/096179 | 5/2018 |
| WO | WO 2018/104540 | 6/2018 |
| WO | WO 2018/167320 | 9/2018 |
| WO | WO 2018/172556 | 9/2018 |
| WO | WO 2018/211038 | 11/2018 |

OTHER PUBLICATIONS

Azarani et al., "RNA analysis by ion-pair reversed-phase high performance liquid chromatography", *Nucl. Acids Res.*, 29(2):E7, 2001.

International Preliminary Report on Patentability issued in corresponding PCT Application No. PCT/EP2017/080703, dated May 28, 2019.

International Search Report and Written Opinion issued in corresponding PCT Application No. PCT/EP2017/080703, dated Feb. 5, 2018.

Matos et al., "Plasmid DNA purification using a multimodal chromatography resin", *J. Mol. Recognit.*, 27(4):184-189, 2014.

* cited by examiner

SEQUENCE LISTING

```
<160> NUMBER OF SEQ ID NOS: 1

<210> SEQ ID NO 1
<211> LENGTH: 547
<212> TYPE: RNA
<213> ORGANISM: artificial
<220> FEATURE:
<223> OTHER INFORMATION: RNA obtained by in vitro transcription

<400> SEQUENCE: 1
gggagaaagc ucaagcuuau ccaaguaggc uggucaccug uacaacguag ccgguauuuu      60 uuuuuuuuu uuuuuuuga ccgucucaag guccaaguua gucugccuau aaaggugcgg     120
auccacagcu gaugaaagac uugugcggua cgguuaaucu ccccuuuuuu uuuuuuuuu     180 uuuuuaguaa augcgucuac ugaauccagc gaugaugcug gcccagaucu ucgaccacaa     240
gugcauauag uagucaucga gggucgccuu uuuuuuuuu uuuuuuuuu uggcccaguu     300 cugagacuuc gcuagagacu acaguuacag cugcaguagu aaccacugcg gcuauugcag     360
gaaaucccgu ucagguuuuu uuuuuuuuu uuuuuccgc ucacuaugau uaagaaccag     420
guggaguguc acugcucucg aggucucacg agagcgcucg auacaguccu uggaagaauc     480 uuuuuuuuu uuuuuuuuu uugugcgacg aucacagaga acuucuauuc augcaggucu     540
gcucuag                                                              547
```

METHOD FOR PURIFYING RNA

This invention was made with government support under HR0011-11-3-0001 awarded by the Defense Advanced Research Projects Agency. The government has certain rights in the invention.

This application is a national phase application under 35 U.S.C. § 371 of International Application No. PCT/EP2017/080703, filed Nov. 28, 2017, which claims benefit of International Application No. PCT/EP2016/079026, filed Nov. 28, 2016, the entire contents of each of which are hereby incorporated by reference.

FIELD OF THE INVENTION

The present invention relates to methods for purifying RNA by chromatography under high salt conditions, e.g. by hydrophobic interaction chromatography.

BACKGROUND OF THE INVENTION

RNA is emerging as an innovative candidate for a variety of pharmaceutical applications, but efficient purification of RNA is still a challenge. This is partly due to the different types and combinations of undesired contaminants in a sample that need to be separated from a desired RNA species to obtain a pure RNA sample. Such contaminants are typically components and by-products of any upstream processes, for example RNA manufacture. If RNA in vitro transcription is used to produce large RNA molecules, the sample after transcription typically contains the desired RNA species and various contaminants such as undesired RNA species, various proteins, spermidine, DNA template or fragments thereof, pyrophosphates, free nucleotides, endotoxins, detergents, and organic solvents.

Commercial downstream applications (e.g. formulation procedures and/or use as a pharmaceutical composition and/or vaccine) pose further constraints on any purification method for RNA requiring (i) a high degree of purity while retaining RNA stability and functionality; (ii) compatibility with any formulation requirements of the RNA for in vivo delivery; and (iii) compliance with good manufacturing practices. Furthermore, in order to meet industrial applicability, any RNA purification method must enable consistent, cost- and time-efficient, as well as quick, easy, reproducible, repetitive, cleanable (cleaning-in place), and scalable (large scale, small scale) operation.

A common laboratory technique is RNA precipitation, allowing for sample concentration as well as depletion of contaminating high molecular weight contaminants and low molecular weight contaminants such as proteins and spermidine, respectively. However, precipitation is not the method of choice in industrial production processes since precipitation and re-solubilisation of nucleic acids is time-consuming. Moreover, the use of alcohols and other organic solvents should be avoided in a highly regulated environment, e.g. current good manufacturing processes (cGMP). Moreover, the use of silica-based columns for RNA purification has the disadvantage that silica based materials do not allow cleaning with common cleaning solutions such as NaOH etc. as silica materials are not compatible with alkaline buffers commonly used for cleaning (cleaning in place).

Other processes for the purification of RNA are described in the art as outlined below.

WO 03/051483 A1 describes a method for purifying a polynucleotide by a chromatographic process comprising a combination of steps which are based on different chromatographic principles, such as hydrophobic interaction chromatography, polar interaction chromatography and anion exchange chromatography.

WO 2008/077592 discloses a method for purifying RNA with ion-pairing reverse phase HPLC on a preparative scale using a porous reversed stationary phase. It is reported that a particular advantage of using the specified porous stationary phase is that excessively high pressures can be avoided, facilitating a preparative purification of RNA.

WO 2014/140211, WO 2014/152966 and PCT/EP2016/062152 disclose methods of purifying RNA by means of tangential flow filtration. However, such a method is only suitable for large-scale preparations and technically not appropriate for small scale-preparations.

Hence, there remains a need for further RNA purification methods, and in particular, for those that allow cost- and time-efficient purification of RNAs at various scale with high yield and pharmaceutical-grade purity, stability, and shelf life. Said further purification methods should ideally allow for a cleaning of the RNA preparation (e.g., depletion of contaminants from crude preparations), for a polishing of RNA preparations (e.g., depletion of residual contaminants such as solvents etc. from purified RNA preparation), for a concentration of the RNA preparation, for capturing an RNA of an RNA preparation, and for a conditioning of the RNA preparation (e.g., re-buffering). In particular, methods are required that are executable in a regulated environment (e.g., cGMP) and that are scalable, allowing for both small-scale and large-scale RNA preparations. Specifically, methods are needed to allow RNA purification in a small-scale manufacturing process that can be e.g. used in high throughput screening approaches or in the production of small amounts of pharmaceutical-grade RNA e.g. for personalized therapies. Further, methods are needed to allow RNA purification using materials compatible with common alkaline cleaning solutions. For large-scale preparations the method should allow for operations at large flow rates.

It is thus an object of the present invention to provide further RNA purification methods.

SUMMARY OF THE INVENTION

The inventors surprisingly found that applying a crude RNA in vitro transcription reaction mixture (including enzymes and proteins such as RNA polymerase, spermidine, desired RNA products, abortive RNA products, DNA template, NTPs etc.) or HPLC purified RNA under high salt conditions to a monolithic column with hydroxyl ligands led to binding of the desired RNA to the respective column support material and to depletion of undesired contaminants (enzymes, proteins etc.).

In addition, the inventors surprisingly found that applying HPLC purified RNA under high salt conditions to a column having a sulfate ($SO_3$) ligand which column is typically used for cation exchange chromatography also led to binding of the desired RNA to the respective column support material and to depletion of undesired contaminants (spermidine etc.).

Hence, the method of the present invention may be used for purifying and/or re-buffering and/or concentrating and/or polishing and/or capturing of a crude in vitro transcription mixture, an eluate from a RP-HPLC column containing RNA, or already purified RNA (e.g., HPLC purified RNA) or other RNA preparations (e.g., cellular RNA preparations).

Accordingly, the present invention relates to a method for purifying RNA, comprising the steps of:

a) applying a sample containing RNA in an equilibration buffer having a high salt concentration to a support material capable of binding the RNA under high salt conditions, wherein the support comprises hydroxyl or sulfate groups;
b) optionally, washing the support material with a washing buffer having a high salt concentration; and
c) eluting the nucleic acid from the support material with an elution solution.

In one embodiment, the method does not comprise a polar interaction chromatography or an anion exchange chromatography step.

Preferably, the RNA is in vitro transcribed RNA.

In one embodiment, the equilibration buffer and/or the washing buffer has a salt concentration of 50 mM to 5 M.

In one embodiment, the equilibration buffer and/or the washing buffer comprises sodium chloride or ammonium sulfate.

In one embodiment, the equilibration buffer and/or the washing buffer comprises 2 M NaCl.

In one embodiment, the equilibration buffer and/or the washing buffer comprises 20 mM HEPES-NaOH, pH 7.0, 2 M NaCl.

In one embodiment, the equilibration buffer and the washing buffer have the same composition and the same pH.

The support material may be a monolithic support material.

In one embodiment the support material is a methacrylate polymer.

The hydroxyl ligand or sulfate moiety may be attached directly to the support material.

The RNA may be eluted by gradually decreasing the salt concentration.

In one embodiment the elution solution does not contain a salt.

In one embodiment the elution solution comprises 20 mM HEPES-NaOH, pH 7.0.

The present invention further relates to a method for purifying in vitro transcribed RNA, comprising the steps of:
a) transcribing RNA from a template DNA in vitro;
b) applying a sample containing the in vitro transcribed RNA in an equilibration buffer having a high salt concentration to a support material capable of binding the RNA under high salt conditions;
c) optionally, washing the support material with a washing buffer having a high salt concentration; and
d) eluting the RNA from the support material with an elution solution.

The method may further comprise a step a1) of degrading the template DNA, wherein the template DNA may be degraded by treatment with DNase.

The method may further comprise a step a2) of subjecting the in vitro transcribed RNA to an RP-HPLC step and/or a step e) of preparing a pharmaceutical composition comprising said RNA.

In one embodiment the equilibration buffer and/or the washing buffer has a salt concentration of 50 mM to 5 M.

In one embodiment the equilibration buffer and/or the washing buffer comprises sodium chloride or ammonium sulfate.

In one embodiment the equilibration buffer and/or the washing buffer comprises 2 M NaCl.

In one embodiment the equilibration buffer and/or the washing buffer comprises 20 mM HEPES-NaOH, pH 7.0, 2 M NaCl.

In one embodiment the equilibration buffer and the washing buffer have the same composition and the same pH.

The support material may be a monolithic support material.

The support material may be a methacrylate polymer.

Preferably, the support material comprises a ligand capable of binding the RNA and the ligand may be a hydroxyl ligand or a sulfate moiety. Preferably, the hydroxyl ligand or sulfate moiety is attached directly to the support material.

The RNA may be eluted by gradually decreasing the salt concentration.

In one embodiment the elution solution does not contain a salt.

In one embodiment the elution buffer comprises 20 mM HEPES-NaOH, pH 7.0.

The present invention also relates to a method for purifying in vitro transcribed RNA, comprising the steps of:
a) transcribing RNA from a template DNA in vitro;
b) degrading the template DNA;
c) subjecting the in vitro transcribed RNA to an RP-HPLC step;
d) applying the eluate from the RP-HPLC in an equilibration buffer having a high salt concentration to a support material capable of binding the RNA under high salt conditions;
e) washing the support material with a washing buffer having a high salt concentration; and
f) eluting the RNA from the support material with an elution solution.

The method may further comprise a step g) of preparing a pharmaceutical composition comprising said RNA.

The template DNA may be degraded by treatment with DNase.

In one embodiment the equilibration buffer and/or the washing buffer has a salt concentration of 50 mM to 5 M.

In one embodiment the equilibration buffer and/or the washing buffer comprises sodium chloride or ammonium sulfate.

In one embodiment the equilibration buffer and/or the washing buffer comprises 2 M NaCl.

In one embodiment the equilibration buffer and/or the washing buffer comprises 20 mM HEPES-NaOH, pH 7.0, 2 M NaCl.

In one embodiment the equilibration buffer and the washing buffer have the same composition and the same pH.

The support material may be a monolithic support material.

The support material may be a methacrylate polymer.

Preferably, the support material comprises a ligand capable of binding the RNA and the ligand may be a hydroxy ligand or a sulfate moiety. Preferably, the hydroxyl ligand or sulfate moiety is attached directly to the support material.

The RNA may be eluted by gradually decreasing the salt concentration.

In one embodiment the elution solution does not contain a salt.

In one embodiment the elution buffer comprises 20 mM HEPES-NaOH, pH 7.0.

The present invention also relates to a method for purifying in vitro transcribed RNA, comprising the steps of:
a) transcribing RNA from a template DNA in vitro;
b) degrading the template DNA;
c) subjecting the in vitro transcribed RNA to an RP-HPLC step;
d) removing organic solvent from the eluate of the RP-HPLC step;

e) applying the purified RNA in an equilibration buffer having a high salt concentration to a support material capable of binding the RNA under high salt conditions;
f) washing the support material with a washing buffer having a high salt concentration; and
g) eluting the RNA from the support material with an elution solution.

The method may further comprise a step h) of preparing a pharmaceutical composition comprising said RNA.

The template DNA may be degraded by treatment with DNase.

In one embodiment the equilibration buffer and/or the washing buffer has a salt concentration of 50 mM to 5 M.

In one embodiment the equilibration buffer and/or the washing buffer comprises sodium chloride or ammonium sulfate.

In one embodiment the equilibration buffer and/or the washing buffer comprises 2 M NaCl.

In one embodiment the equilibration buffer and/or the washing buffer comprises 20 mM HEPES-NaOH, pH 7.0, 2 M NaCl.

In one embodiment the equilibration buffer and the washing buffer have the same composition and the same pH.

The support material may be a monolithic support material.

The support material may be a methacrylate polymer.

Preferably, the support material comprises a ligand capable of binding the RNA and the ligand may be a hydroxy ligand or a sulfate moiety. Preferably, the hydroxyl ligand or sulfate moiety is attached directly to the support material.

The RNA may be eluted by gradually decreasing the salt concentration.

In one embodiment the elution solution does not contain a salt.

In one embodiment the elution buffer comprises 20 mM HEPES-NaOH, pH 7.0.

The present invention further relates to a method for purifying in vitro transcribed RNA, comprising the steps of:
a) transcribing RNA from a template DNA in vitro;
b) applying a sample containing the in vitro transcribed RNA in an equilibration buffer comprising 20 mM HEPES-NaOH, pH 7.0 and 2 M NaCl to a monolithic support comprising a hydroxyl or a sulfate moiety;
c) washing the support material with said equilibration buffer; and
d) eluting the RNA from the support material by a gradually decreasing salt gradient using an elution buffer comprising 20 mM HEPES-NaOH, pH 7.0.

The present invention also relates to a method for purifying in vitro transcribed RNA, comprising the steps of:
a) transcribing RNA from a template DNA in vitro;
b) degrading the template DNA by DNase treatment;
c) subjecting the in vitro transcribed RNA to an RP-HPLC step;
d) applying the eluate from the RP-HPLC in an equilibration buffer comprising 20 mM HEPES-NaOH, pH 7.0 and 2 M NaCl to a monolithic support comprising a hydroxyl or a sulfate moiety;
e) washing the support material with said equilibration buffer; and
f) eluting the RNA from the support material by a gradually decreasing salt gradient using an elution buffer comprising 20 mM HEPES-NaOH, pH 7.0.

The method may further comprise a step g) of preparing a pharmaceutical composition comprising said RNA.

The present invention also relates to a method for purifying in vitro transcribed RNA, comprising the steps of:
a) transcribing RNA from a template DNA in vitro;
b) degrading the template DNA by DNase treatment;
c) subjecting the in vitro transcribed RNA to an RP-HPLC step;
d) removing organic solvent from the eluate of the RP-HPLC step;
e) applying the eluate from the RP-HPLC in an equilibration buffer comprising 20 mM HEPES-NaOH, pH 7.0 and 2 M NaCl to a monolithic support comprising a hydroxyl or a sulfate moiety;
f) washing the support material with said equilibration buffer; and
g) eluting the RNA from the support material by a gradually decreasing salt gradient using an elution buffer comprising 20 mM HEPES-NaOH, pH 7.0.

The method may further comprise a step h) of preparing a pharmaceutical composition comprising said RNA.

Definitions

For the sake of clarity and readability, the following definitions are provided. Any technical feature mentioned for these definitions may be read on each and every embodiment of the invention. Additional definitions and explanations may be specifically provided in the context of these embodiments. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document.

Purification: The term "purification" or "purifying" is understood to mean that the desired RNA in a sample is separated and/or isolated from the impurities present therein. Thus, after subjecting the RNA to the method of the present invention the RNA is present in a purer form than in the RNA-containing sample before subjecting it to the method of the present invention. Undesired constituents of RNA-containing samples which therefore need to be separated may in particular be enzymes such as RNA polymerase, other proteins, spermidine, and nucleotides.

Using the method according to the invention, RNA is purified which has a higher purity after purification than the starting material. It is desirable in this respect for the degree of purity to be as close as possible to 100%. A degree of purity of more than 70%, in particular 80%, very particularly 90% and most favorably 99% or more may be achieved in this way. The degree of purity may for example be determined by an analytical HPLC, wherein the percentage provided above corresponds to the ratio between the area of the peak for the target RNA and the total area of all peaks representing the by-products.

RNA, mRNA: RNA is the usual abbreviation for ribonucleic acid. It is a nucleic acid molecule, i.e. a polymer consisting of nucleotide monomers. These nucleotides are usually adenosine-monophosphate (AMP), uridine-monophosphate (UMP), guanosine-monophosphate (GMP) and cytidine-monophosphate (CMP) monomers or analogs thereof, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA sequence. Usually RNA may be obtainable by transcription of a DNA sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA.

Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, an open reading frame, optionally a 3'UTR and a poly(A) sequence.

In addition to messenger RNA, several non-coding types of RNA exist which may be involved in regulation of transcription and/or translation, and immunostimulation. The term "RNA" further encompasses RNA molecules, such as viral RNA, retroviral RNA and replicon RNA, small interfering RNA (siRNA), antisense RNA, CRISPR/Cas9 guide RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA). Further the term may encompass circular RNA (circRNA), wherein the circRNA is preferably a protein-coding circRNA.

Modified nucleoside triphosphate: The term "modified nucleoside triphosphate" as used herein refers to chemical modifications comprising backbone modifications as well as sugar modifications or base modifications. These modified nucleoside triphosphates are herein also called (nucleotide) analogs.

In this context, the modified nucleoside triphosphates as defined herein are nucleotide analogs/modifications, e.g. backbone modifications, sugar modifications or base modifications. A backbone modification in connection with the present invention is a modification, in which phosphates of the backbone of the nucleotides are chemically modified. A sugar modification in connection with the present invention is a chemical modification of the sugar of the nucleotides. Furthermore, a base modification in connection with the present invention is a chemical modification of the base moiety of the nucleotides. In this context nucleotide analogs or modifications are preferably selected from nucleotide analogs which are applicable for transcription and/or translation.

Sugar Modifications

The modified nucleosides and nucleotides, which may be used in the context of the present invention, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R═H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH$_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified nucleotide can include nucleotides containing, for instance, arabinose as the sugar.

Backbone Modifications

The phosphate backbone may further be modified in the modified nucleosides and nucleotides. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications

The modified nucleosides and nucleotides, which may be used in the present invention, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In some embodiments, the nucleotide analogs/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O—(I-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O—(I-Thiophosphate)-Pseudouridine.

In further specific embodiments the modified nucleotides include nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Further modified nucleotides have been described previously (WO 2013/052523).

Sample: As used herein, the term "sample" refers to a liquid composition comprising the RNA to be purified and one or more impurities. The sample may be the in vitro transcription mixture or it may be a partially purified sample. For example, the sample may have already been subjected to any known RNA purification technique, in particular to an RP-HPLC purification step and/or precipitation steps.

Impurity/impurities: The term "impurity" includes any molecule present in the sample containing RNA other than the RNA to be purified. In particular, it includes components of the RNA in vitro transcription reaction such as enzymes, proteins and nucleotides.

Equilibration buffer: The term "equilibration buffer" refers to a salt solution which is used to prepare the support material for loading the sample containing RNA. Within the method of the present invention the equilibration buffer is also used to load the sample containing RNA on the support material. Therefore, it is passed through the support material simultaneously or substantially simultaneously with passage of the sample through the support material. In certain embodiments, the equilibration buffer is combined with the sample containing RNA prior to passage through the support material.

Support material: In chromatographic processes the support material is typically a material which serves as the stationary phase, i.e. as a material along which the mobile phase containing the molecules to be separated, in the present case the equilibration buffer with the sample containing RNA, moves. The support material can be functionalized with ligands which are suitable for the kind of separation desired. For example, for ion exchange chromatography the support material may be functionalized with positively or negatively charged ligands and for hydrophobic interaction chromatography the support material may be functionalized with hydrophobic ligands such as alkyl groups, aryl groups or combinations thereof.

The most widely used support materials are hydrophilic carbohydrates such as cross-linked agarose and synthetic copolymer materials and methacrylate based connective interaction media (CIM) monolithic columns. The support material may also comprise derivatives of cellulose, polystyrene, synthetic poly amino acids, synthetic polyacrylamide gels, cross-linked dextran or a glass surface.

For hydrophobic interaction chromatography or purification under high salt conditions a hydrophobic ligand such as $NH_2$, $SO_3H$, $PO_4H_2$, SH, imidazoles, phenolic groups, butyl, hexyl, phenyl, octyl, polypropylene glycol or non-ionic radicals such as OH and $CONH_2$ may be attached to the support material. These hydrophobic ligands may be attached using difunctional linking groups such as —NH—, —S— and —COO. Within the present invention, the use of OH and $SO_3$ ligands is particularly preferred.

In some embodiments, the support material may be selected from the group consisting of an agarose media or a membrane functionalized with phenyl groups (e.g., Phenyl Sepharose™ from GE Healthcare or a Phenyl Membrane from Sartorius), Tosoh Hexyl, CaptoPhenyl, Phenyl Sepharose™ 6 Fast Flow with low or high substitution, Phenyl Sepharose™ High Performance, Octyl Sepharose™ High Performance (GE Healthcare); Fractogel™ EMD Propyl or Fractogel™ EMD Phenyl (E. Merck, Germany); Macro-Prep™ Methyl or Macro-Prep™ t-Butyl columns (Bio-Rad, California); WP HI-Propyl (C3)™ (J. T. Baker, New Jersey) or Toyopearl™ ether, phenyl or butyl (TosoHaas, PA). ToyoScreen PPG, ToyoScreen Phenyl, ToyoScreen Butyl, and ToyoScreen Hexyl are based on rigid methacrylic polymer beads. GE HiScreen Butyl FF and HiScreen Octyl FF are based on high flow agarose based beads. Preferred are Toyopearl Ether-650M, Toyopearl Phenyl-650M, Toyopearl Butyl-650M, Toyopearl Hexyl-650C (TosoHaas, PA), POROS-OH (ThermoFisher) or methacrylate based monolithic columns such as CIM-OH, CIM-SO$_3$, CIM-C4 A and CIM C4 HDL which comprise OH, sulfate or butyl ligands, respectively (BIA Separations).

The support material is preferably present in a column, wherein the sample containing RNA is loaded on the top of the column and the eluent is collected at the bottom of the column.

Washing buffer: The term "washing buffer", as used herein refers to a buffer which is passed through the support material after loading the sample containing RNA and before eluting the RNA. The washing buffer therefore serves to remove impurities from the support material before the RNA is eluted.

Elution solution: An elution solution is used to disrupt the interaction between the RNA and the support material. Accordingly, the elution solution has a lower salt concentration than the equilibration buffer and the washing buffer.

Anion exchange chromatography: In anion exchange chromatography binding to a support material is achieved by electrostatic interaction of negatively charged sample components with positively charged moieties such as diethylaminoethyl (DEAE) or quaternary ammonium (QA) on the surface of the support material. This interaction typically occurs at low salt concentrations and elution is achieved by increasing the salt concentration.

Polar interaction chromatography: Polar interaction chromatography or hydrophilic interaction chromatography (HILIC) is based on the interaction of components of a sample with a support material which carries polar functional groups such as hydroxyl or amine. The interaction may occur at high salt concentrations in the presence of an organic solvent, in particular acetonitrile.

Hydrophobic interaction chromatography: Hydrophobic interaction chromatography is based on the hydrophobic interaction between hydrophobic moieties bound to a support material and hydrophobic regions of the molecule that binds to the matrix such as RNA. Binding is achieved at high salt concentrations and the molecule is eluted from the matrix by decreasing the salt concentration and, optionally, the addition of organic solvents.

In vitro transcription: The terms "in vitro transcription" or "RNA in vitro transcription" relate to a process wherein RNA is synthesized in a cell-free system (in vitro). DNA, particularly plasmid DNA, a PCR amplified DNA or synthetic DNA, is used as template for the generation of RNA transcripts. RNA may be obtained by DNA-dependent in vitro transcription of an appropriate DNA template, which according to the present invention is preferably a linearized plasmid DNA template. The promoter for controlling in vitro transcription can be any promoter for any DNA-dependent RNA polymerase. Particular examples of DNA-dependent RNA polymerases are the T7, T3, and SP6 RNA polymerases. A DNA template for in vitro RNA transcription may be obtained by cloning of a nucleic acid, in particular cDNA corresponding to the respective RNA to be in vitro transcribed, and introducing it into an appropriate vector for in vitro transcription, for example into plasmid DNA. In a preferred embodiment of the present invention the DNA template is linearized with a suitable restriction enzyme, before it is transcribed in vitro. The cDNA may be obtained by reverse transcription of mRNA or chemical synthesis. Moreover, the DNA template for in vitro RNA synthesis may also be obtained by gene synthesis or PCR.

Methods for in vitro transcription are known in the art (Geall et al. (2013) Semin. Immunol. 25(2): 152-159; Brunelle et al. (2013) Methods Enzymol. 530:101-14). Reagents used in said method typically include:
1) a DNA template with a promoter sequence that has a high binding affinity for its respective RNA polymerase such as bacteriophage-encoded RNA polymerases;
2) ribonucleoside triphosphates (NTPs) for the four bases (adenine, cytosine, guanine and uracil);
3) optionally a cap analog as defined below (e.g. m7G(5') ppp(5')G (m7G));
4) a DNA-dependent RNA polymerase capable of binding to the promoter sequence within the linearized DNA template (e.g. T7, T3 or SP6 RNA polymerase);
5) optionally a ribonuclease (RNase) inhibitor to inactivate any contaminating RNase;
6) optionally a pyrophosphatase to degrade pyrophosphate, which may inhibit transcription;
7) MgCl$_2$, which supplies Mg$^{2+}$ ions as a co-factor for the polymerase;
8) a buffer to maintain a suitable pH value, which can also contain antioxidants (e.g. DTT), amines such as betaine and/or polyamines such as spermidine at optimal concentrations.

"In vitro transcribed RNA" is an RNA which has been prepared by the process of in vitro transcription as described above.

DNA template: The DNA template provides the nucleic acid sequence which is transcribed into the RNA by the process of in vitro transcription and which therefore comprises a nucleic acid sequence which is complementary to the RNA sequence which is transcribed therefrom. In addition to the nucleic acid sequence which is transcribed into the RNA the DNA template comprises a promoter to which the RNA polymerase used in the in vitro transcription process binds with high affinity.

Preferably, the DNA template may be a linearized plasmid DNA template. The linear template DNA is obtained by contacting plasmid DNA with a restriction enzyme under suitable conditions so that the restriction enzyme cuts the plasmid DNA at its recognition site(s) and disrupts the circular plasmid structure. The plasmid DNA is preferably cut immediately after the end of the sequence which is to be transcribed into RNA. Hence, the linear template DNA comprises a free 5' end and a free 3' end which are not linked to each other. If the plasmid DNA contains only one recognition site for the restriction enzyme, the linear template DNA has the same number of nucleotides as the plasmid DNA. If the plasmid DNA contains more than one recognition site for the restriction enzyme, the linear template DNA has a smaller number of nucleotides than the plasmid DNA. The linear template DNA is then the fragment of the plasmid DNA which contains the elements necessary for in vitro transcription, that is a promotor element for RNA transcription and the template DNA element. The open reading frame of the linear template DNA determines the sequence of the transcribed RNA by the rules of base-pairing.

In other embodiments, the DNA template may be selected from a synthetic double stranded DNA construct, a single-stranded DNA template with a double-stranded DNA region comprising the promoter to which the RNA polymerase binds, a cyclic double-stranded DNA template with promoter and terminator sequences or a linear DNA template amplified by PCR or isothermal amplification.

Monolithic support material: A monolithic support material (or monolithic bed) is a continuous bed consisting of a single piece of a highly porous solid material where the pores are highly interconnected forming a network of flow-through channels. Hence, the void volume is decreased to a minimum and all the mobile phase is forced to flow through the large pores of the medium.

Three types of monolithic support materials are commercially available:
1) Silica gel based monolithic beds which are solid rods of silica monolith that have been prepared according to a sol-gel process. This process is based on the hydrolysis and polycondensation of alkoxysilanes in the presence of water-soluble polymers. The method leads to "rods" made of a single piece of porous silica with a defined bimodal pore structure having macro (of about 2 µm) and mesopores (of about 0.013 µm) when smaller rods intended for analytical purposes are prepared.
2) Polyacrylamide based monolithic beds are made of swollen polyacrylamide gel compressed in the shape of columns. Their technology relies on the polymerization of advanced monomers and ionomers directly in the chromatographic column. In the presence of salt, the polymer chains form aggregates into large bundles by hydrophobic interaction, creating voids between the bundles (irregularly shaped channels) large enough to permit a high hydrodynamic flow.
3) Rigid organic gel based monolithic beds: These supports are prepared by free radical polymerization of a mixture of a polymerizable monomer, optionally with functional groups, such as glycidyl methacrylate, ethylene dimethacrylate, a crosslinking agent, a radical chain initiator, such as 2,2'-azobisisobutyronitrile, and porogenic solvents (cyclohexanol and dodecanol) in barrels of an appropriate mold (Svec F, Tennikova TB (1991) J Bioact Compat Polym 6: 393; Svec F, Jelinkova M, Votavova E (1991) Angew Macromol Chem 188: 167; Svec F, Frechet JMJ (1992) Anal Chem 64: 820) in the case of glycidyl methacrylate-co-ethylene dimethacrylate (GMA-EDMA) monoliths.

DNase: DNases are enzymes which hydrolyze DNA by that catalyzing the hydrolytic cleavage of phosphodiester linkages in the DNA backbone. Suitable DNases are isolated from bovine pancreas and are available from various suppliers such as Sigma-Aldrich, New England Biolabs, Qiagen and ThermoFisher. Preferably, the used DNase is free of any RNAse activity. In one embodiment the treatment with DNase is performed in DNase buffer additionally comprising a suitable amount of calcium chloride, such as 0.66 mM $CaCl_2$. The DNA is treated with the DNase for 1 to 5 hours, preferably for 1.5 to 3 hours and more preferably for 2 hours. The DNase treatment is preferably performed at a temperature of 37° C. In one particular embodiment, the DNA template is removed by addition of 0.66 mM $CaCl_2$ and 300 U/ml DNase I in digestion buffer and incubation for two hours at 37° C. The DNase treatment can be stopped by adding EDTA or another chelating agent. Preferably, the DNase treatment is stopped by adding EDTA to a final concentration of 25 mM.

HPLC: HPLC is the common abbreviation of the term "high performance liquid chromatography". In the HPLC process a pressurized liquid solvent containing the sample mixture is passed through a column filled with a solid adsorbent material leading to the interaction of components of the sample with the adsorbent material. Since different components interact differently with the adsorbent material, this leads to the separation of the components as they flow out of the column. The operational pressure in HPLC process is typically between 50 and 350 bar. The term HPLC includes reversed phase HPLC (RP-HPLC), size exclusion chromatography, gel filtration, affinity chromatography, hydrophobic interaction chromatography or ion pair chromatography, wherein reversed phase HPLC is preferred.

Reversed phase HPLC (RP-HPLC): Reversed phase HPLC uses a non-polar stationary phase and a moderately polar mobile phase and therefore works with hydrophobic interactions which result from repulsive forces between a relatively polar solvent, the relatively non-polar analyte, and the non-polar stationary phase (reversed phase principle). The retention time on the column is therefore longer for molecules which are more non-polar in nature, allowing polar molecules to elute more readily. The retention time is increased by the addition of polar solvent to the mobile phase and decreased by the addition of more hydrophobic solvent.

The characteristics of the specific RNA molecule as an analyte may play an important role in its retention characteristics. In general, an analyte having more apolar functional groups results in a longer retention time because it increases the molecule's hydrophobicity and therefore the interaction with the non-polar stationary phase. Very large molecules, however, can result in incomplete interaction between the large analyte surface and the alkyl chain. Retention time increases with hydrophobic surface area which is roughly inversely proportional to solute size. Branched chain compounds elute more rapidly than their corresponding isomers because the overall surface area is decreased.

Ion-pair, reversed-phase HPLC: Ion-pair, reversed-phase HPLC is a specific form of reversed-phase HPLC in which an ion with a lipophilic residue and positive charge such as an alkylammonium salt, e.g. triethylammonium acetate, is added to the mobile phase as counter ion for the negatively charged RNA. When used with common hydrophobic HPLC phases in the reversed-phase mode, ion pair reagents can be used to selectively increase the retention of the RNA.

Pharmaceutical composition: A pharmaceutical composition is a composition comprising a pharmaceutically active agent such as a therapeutic RNA and one or more pharmaceutically acceptable carriers. A pharmaceutical composition is suitable for storage for a certain period of time and for administration to a patient. The pharmaceutical composition may be in liquid or in freeze-dried form. A suitable injection solution for RNA is disclosed in WO 2006/122828 A2. A method for lyophilizing RNA is described in WO 2016/165831 A1. The pharmaceutical composition comprises the RNA in a pharmaceutically effective amount which is able to exert the therapeutic effect. The RNA may be complexed using cationic and/or polycationic compounds such as polycationic peptides or polymers (see, e.g., WO 2009/030481 A1; WO 2012/013326 A1; WO 2013/113501 A1; WO 2013/113736 A1) or may be encapsulated (e.g., lipid nanoparticles (LNPs), liposomes).

DETAILED DESCRIPTION OF THE INVENTION

As discussed above, the present invention is based on the finding that RNA can be purified either from a crude in vitro transcription mixture or from an RP-HPLC-purified mixture by a chromatography step wherein the RNA binds to the support material or the moiety attached thereto under high salt conditions and is then eluted by decreasing the salt concentration. These conditions are also used in hydrophobic interaction chromatography so that the method of the present invention may involve hydrophobic interaction chromatography, although the support material used in the method of the present invention is not restricted to the material typically used in hydrophobic interaction chromatography, but may also comprise material which is typically used in other chromatographic techniques such as ion exchange chromatography. One example of such a material is a support material with sulfate groups. In the present invention the binding of the RNA to the support material does not involve the interaction between nucleotide bases within the RNA and nucleotide bases attached to the support, in particular the binding of the RNA to the support material does not involve the interaction between the polyA tail of the RNA and thymidines attached to the support.

Hence, in a first aspect, the present invention relates to a method for purifying RNA, comprising the steps of:
a) applying a sample containing RNA in an equilibration buffer having a high salt concentration to a support material capable of binding the RNA under high salt conditions, wherein the support comprises hydroxyl or sulfate groups;
b) washing the support material with a washing buffer having a high salt concentration; and
c) eluting the nucleic acid from the support material with an elution solution,
wherein the method does not comprise a polar interaction chromatography or an anion exchange chromatography step.

In another aspect the present invention relates to a method for purifying in vitro transcribed RNA, comprising the steps of:
a) transcribing RNA from a template DNA in vitro;
b) applying a sample containing the in vitro transcribed RNA in an equilibration buffer having a high salt concentration to a support material capable of binding the RNA under high salt conditions, wherein the support comprises hydroxyl or sulfate groups;
c) washing the support material with a washing buffer having a high salt concentration; and
d) eluting the RNA from the support material with an elution solution.

Before applying the sample containing RNA or in vitro transcribed RNA to the support material, the sample may be diluted, for example with equilibration buffer. Preferably, the sample is diluted between 1:2 and 1:20, more preferably it is diluted between 1:5 and 1:12 and most preferably it is diluted 1:10, i.e. one volume of the sample is mixed with 9 volumes of equilibration buffer. In other embodiments, the sample containing RNA or in vitro transcribed RNA is not diluted with equilibration buffer before applying the sample to the support material.

In the process of the present invention, any monolithic support can be used which is permeable for RNA. Preferably, the monolithic support is based on a methacrylate polymer, more preferably it is based on poly(glycidyl methacrylate-co ethylene dimethylacrylate). The average pore radius is preferably 500 to 1200 nm, preferably it is 675 nm. Also preferably the monolithic support is CIM available from BIA Separations.

As described above, the monolithic bed may carry functional moieties (ligands) that allow for the specific chromatographic separation. The ligand density is chosen such that capacity, yield and recovery are maximized. Preferably, the monolithic bed comprises a hydroxyl or a sulfate moiety and more preferably it is CIM® OH or CIM® $SO_3$ available from BIA Separations. The hydroxyl moiety is attached to the monolithic bed directly. In particular, the hydroxyl moiety is not part of a ligand carrying additional chemical groups such as the ligand N-benzyl ethanolamine.

The solution applied to the support material has an RNA concentration of 0.05 mg/ml to 5 mg/ml, preferably of 0.07 mg/ml to 3 mg/ml, more preferably of 0.1 mg/ml to 1 mg/ml or 0.1 mg/ml to 0.5 mg/ml and most preferably the RNA concentration is 0.2 mg/ml.

The equilibration buffer has a high salt concentration to enhance the interaction of the RNA with the support material or the ligand attached thereto. Preferably, the high salt concentration is from 50 mM to 5 M or from 100 mM to 4 M, more preferably, the salt concentration is from 300 mM to 3.5 M or from 500 mM to 3 M, even more preferably the high salt concentration is from 700 mM to 2.8 M or from 1.2 M to 2.5 M and most preferably it is 2 M, depending, in part, on the salt type. In one embodiment the high salt concentration is 1 M, 1.1 M, 1.2 M, 1.3 M, 1.4 M, 1.5 M, 1.6 M, 1.7 M, 1.8 M, 1.9 M, 2.0 M, 2.1 M, 2.2 M, 2.3 M, 2.4 M, 2.5 M, 2.6 M, 2.7 M, 2.8 M, 2.9 M or 3.0 M.

The equilibration buffer may comprise a salt selected from the group consisting of sodium chloride, ammonium sulfate, sodium sulfate, ammonium chloride, sodium bromide, sodium citrate or a combination thereof. In a particular embodiment, the equilibration buffer comprises sodium chloride. The equilibration buffer may comprise a cation selected from the group consisting of $Ba^{2+}$, $Ca^{2+}$, $Mg^{2+}$, $Li^+$, $Cs^+$, $Na^+$, $K^+$, $Rb^+$, and $NH_4^+$, and/or an anion selected from the group consisting of $PO_4^{3-}$, $SO_4^{2-}$, $CH_3CO_3^-$, $Cl^-$, $Br^-$, $NO_3^-$, $ClO_4^-$, $I^-$, and $SCN^-$ or a combination thereof.

In a preferred embodiment the equilibration buffer comprises 2 M sodium chloride.

The pH of the equilibration buffer is between 4.0 and 8.5 or between 5.0 and 8.0. In certain embodiments, the equilibration buffer has a pH between 6.0 and 7.5. Most preferably, the pH of the equilibration buffer is 7.0.

The equilibration buffer may contain a buffer substance which is a weak acid or base used to maintain the acidity (pH) of a solution near a chosen value after the addition of another acid or base. Hence, the function of a buffer substance is to prevent a rapid change in pH when acids or bases are added to the solution. Suitable buffer substances for use in the present invention are HEPES (2-[4-(2-hydroxyethyl)piperazin-1-yl]ethanesulfonic acid), Tris (2-amino-2-hydroxymethyl-propane-1,3-diol), phosphate buffer and acetate buffer.

Most preferably, the equilibration buffer comprises 20 mM HEPES-NaOH, pH 7.0 and 2 M NaCl.

Preferably, the equilibration buffer does not contain 1 mM EDTA and more preferably it does not contain any EDTA at all.

The washing buffer has a high salt concentration so that the interaction of the RNA with the support material or the ligand attached thereto is not interrupted during washing. Preferably, the high salt concentration is from 50 mM to 5 M or from 100 mM to 4 M, more preferably, the salt concentration is from 300 mM to 3.5 M or from 500 mM to 3 M, even more preferably the high salt concentration is from 700 mM to 2.8 M or from 1.2 M to 2.5 M and most preferably it is 2 M, depending, in part, on the salt type. In one embodiment the high salt concentration is 1 M, 1.1 M, 1.2 M, 1.3 M, 1.4 M, 1.5 M, 1.6 M, 1.7 M, 1.8 M, 1.9 M, 2.0 M, 2.1 M, 2.2 M, 2.3 M, 2.4 M, 2.5 M, 2.6 M, 2.7 M, 2.8 M, 2.9 M or 3.0 M.

The washing buffer may comprise a salt selected from the group consisting of sodium chloride, ammonium sulfate, sodium sulfate, ammonium chloride, sodium bromide or a combination thereof. In a particular embodiment, the equilibration buffer comprises sodium chloride. The washing buffer may comprise a cation selected from the group consisting of $Ba^{2+}$, $Ca^{2+}$, $Mg^{2+}$, $Li^+$, $Cs^+$, $Na^+$, $K^+$, $Rb^+$, and $NH_4^+$, and/or an anion selected from the group consisting of $PO_4^{3-}$, $SO_4^{2-}$, $CH_3CO_3^-$, $Cl^-$, $Br^-$, $N_3^-$, $ClO_4^-$, $I^-$, and $SCN^-$ or a combination thereof.

In a preferred embodiment the washing buffer comprises 2 M sodium chloride.

The pH of the washing buffer is between 4.0 and 8.5 or between 5.0 and 8.0. In certain embodiments, the equilibration buffer has a pH between 6.0 and 7.5. Most preferably, the pH of the washing buffer is 7.0.

The washing buffer may contain a buffer substance which is a weak acid or base used to maintain the acidity (pH) of a solution near a chosen value after the addition of another acid or base. Hence, the function of a buffer substance is to prevent a rapid change in pH when acids or bases are added to the solution. Suitable buffer substances for use in the present invention are HEPES (2-[4-(2-hydroxyethyl)piperazin-1-yl]ethanesulfonic acid), Tris (2-amino-2-hydroxymethyl-propane-1,3-diol), phosphate buffer and acetate buffer.

More preferably, the washing buffer has the same composition and pH as the equilibration buffer. Most preferably, the washing buffer comprises 20 mM HEPES-NaOH, pH 7.0 and 2 M NaCl.

Preferably, the washing buffer does not contain 1 mM EDTA and more preferably it does not contain any EDTA at all.

The RNA is eluted from the support material by a gradually decreasing salt gradient. To this end, the percentage of the elution solution which is in contact with the support material is gradually increased, thereby disrupting the interaction between the RNA and the support material.

The flow rate of the elution solution is selected such that good separation of the RNA from the impurities contained in the sample is achieved. The eluent flow rate may amount to from 0.5 ml/min to 5 ml/min, preferably from 1 ml/min to 4 ml/min, more preferably it is 3 ml/min. This flow rate may be established and regulated by a pump.

The eluent flow rate is also dependent on the volume of the used column (CV). The flow rate may amount to from 1.5 CV/min to 15 CV/min, preferably from 3 CV/min to 12 CV/min, more preferably it is 9 CV/min. This flow rate may be established and regulated by a pump.

The elution solution may have a salt concentration of less than 500 mM, if the equilibration buffer and the washing buffer have a salt concentration of at least 1 M. The elution solution may have a salt concentration of less than 200 mM, if the equilibration buffer and the washing buffer have a salt concentration of at least 500 mM. The elution solution may have a salt concentration of less than 100 mM, if the equilibration buffer and the washing buffer have a salt concentration of at least 300 mM. The elution solution may have a salt concentration of less than 50 mM, if the equilibration buffer and the washing buffer have a salt concentration of at least 150 mM. The elution solution may have a salt concentration of less than 20 mM, if the equilibration buffer and the washing buffer have a salt concentration of at least 100 mM.

In one embodiment, the elution solution does not comprise any salt.

In one embodiment, the elution solution is water. In another embodiment, the elution solution comprises a buffer substance selected from the group consisting of HEPES (2-[4-(2-hydroxyethyl)-piperazin-1-yl]ethanesulfonic acid), Tris (2-amino-2-hydroxymethyl-propane-1,3-diol), citrate buffer, phosphate buffer and acetate buffer.

The pH of the elution solution is between 4.0 and 8.5 or between 5.0 and 8.0. In certain embodiments, the elution solution has a pH between 6.0 and 7.5. Most preferably, the pH of the washing buffer is 7.0.

In one embodiment, the elution solution comprises the same buffer substance as the equilibration buffer and/or the washing buffer, but has a lower salt concentration as the equilibration buffer and/or the washing buffer as described above. In one embodiment, the elution solution comprises the same buffer substance as the equilibration buffer and/or the washing buffer, but does not comprise any salt. In one embodiment, the elution solution has the same pH as the equilibration buffer and/or the washing buffer, but has a lower salt concentration as the equilibration buffer and/or the washing buffer as described above. In one embodiment, the elution solution has the same pH as the equilibration buffer and/or the washing buffer, but does not comprise any salt. In one embodiment, the elution solution comprises the same buffer substance as the equilibration buffer and/or the washing buffer and has the same pH as the equilibration buffer and/or the washing buffer, but has a lower salt concentration as the equilibration buffer and/or the washing buffer as described above. In one embodiment, the elution solution comprises the same buffer substance as the equilibration buffer and/or the washing buffer and has the same pH as the equilibration buffer and/or the washing buffer, but does not comprise any salt. In a preferred embodiment the elution solution comprises 20 mM HEPES-NaOH, pH 7.0.

Preferably, the elution solution does not contain 1 mM EDTA and more preferably it does not contain any EDTA at all.

The RNA which is eluted from the support material is preferably detected by UV measurement at 260 nm.

In one embodiment, the method of the present invention comprises an additional purification step, before the RNA is subjected to the chromatography under high salt conditions as claimed herein. The additional purification step is preferably a RP-HPLC step. A particularly preferred method for purifying the target RNA by RP-HPLC is disclosed in WO 2008/077592 A1 and involves a reversed-phase HPLC using a porous reversed phase as stationary phase.

In one embodiment, the HPLC fraction comprising RNA obtained from RP-HPLC is subjected to the chromatography under high salt conditions as claimed herein.

In another embodiment, the HPLC fraction comprising RNA is subjected to a precipitation step to remove acetonitrile and triethylammonium acetate before it is subjected to the chromatography under high salt conditions as claimed herein.

In general, any material known to be used as reverse phase stationary phase, in particular any polymeric material may be used, if that material can be provided in porous form. The stationary phase may be composed of organic and/or inorganic material. Examples for polymers to be used for the purification step of the present invention are (non-alkylated) polystyrenes, (non-alkylated) polystyrenedivinylbenzenes, silica gel, silica gel modified with non-polar residues, particularly silica gel modified with alkyl containing residues, more preferably with butyl-, octyl and/or octadecyl containing residues, silica gel modified with phenylic residues, polymethacrylates, etc.

In a particularly preferred embodiment, the material for the reversed phase is a porous polystyrene polymer, a (non-alkylated) porous polystyrenedivinylbenzene polymer, porous silica gel, porous silica gel modified with non-polar residues, particularly porous silica gel modified with alkyl containing residues, more preferably with butyl-, octyl and/or octadecyl containing residues, porous silica gel modified with phenylic residues, porous polymethacrylates, wherein in particular a porous polystyrene polymer or a non-alkylated (porous) polystyrenedivinylbenzene may be used.

A non-alkylated porous polystyrenedivinylbenzene which is particularly preferred for the RP-HPLC step is one which, without being limited thereto, may have a particle size of 8.0±1.5 μm, in particular 8.0±0.5 μm, and a pore size of 1000-1500 Å, in particular 1000-1200 Å or 3500-4500 Å.

The stationary phase is conventionally located in a column. V2A steel is conventionally used as the material for the column, but other materials may also be used for the column provided they are suitable for the conditions prevailing during HPLC. Conventionally the column is straight. It is favourable for the HPLC column to have a length of 5 cm to 100 cm and a diameter of 4 mm to 25 mm. Columns used for the purification step of the method of the invention may in particular have the following dimensions: 50 mm long and 7.5 mm in diameter or 50 mm long and 4.6 mm in diameter, or 50 mm long and 10 mm in diameter or any other dimension with regard to length and diameter, which is suitable for preparative recovery of RNA, even lengths of several meters and also larger diameters being feasible in the case of upscaling.

The HPLC is preferably performed as ion-pair, reversed phase HPLC as defined above.

In a preferred embodiment, a mixture of an aqueous solvent and an organic solvent is used as the mobile phase for eluting the RNA. Preferably, the buffer used as the aqueous solvent has a pH of 6.0-8.0, for example of about 7, for example 7.0. More preferably the buffer is triethylammonium acetate which preferably has a concentration of 0.02 M to 0.5 M, more preferably of 0.08 M to 0.12 M. Most preferably, an 0.1 M triethylammonium acetate buffer is used, which also acts as a counter ion to the RNA in the ion pair method.

In a preferred embodiment, the organic solvent which is used in the mobile phase is selected from acetonitrile, methanol, ethanol, 1-propanol, 2-propanol and acetone or a mixture thereof. More preferably it is acetonitrile.

In a particularly preferred embodiment, the mobile phase is a mixture of 0.1 M triethylammonium acetate, pH 7, and acetonitrile.

Preferably, the mobile phase contains 5.0 vol. % to 25.0 vol. % organic solvent, relative to the mobile phase, and for this to be made up to 100 vol. % with the aqueous solvent. Typically, in the event of gradient separation, the proportion of organic solvent is increased, in particular by at least 10%, more preferably by at least 50% and most preferably by at least 100%, optionally by at least 200%, relative to the initial vol. % in the mobile phase. In a preferred embodiment, the proportion of organic solvent in the mobile phase amounts in the course of HPLC separation to 3 to 9, preferably 4 to 7.5, in particular 5.0 vol. %, in each case relative to the mobile phase. More preferably, the proportion of organic solvent in the mobile phase is increased in the course of HPLC separation from 3 to 9, in particular 5.0 vol. % to up to 20.0 vol. %, in each case relative to the mobile phase. Still more preferably, the method is performed in such a way that the proportion of organic solvent in the mobile phase is increased in the course of HPLC separation from 6.5 to 8.5, in particular 7.5 vol. %, to up to 17.5 vol. %, in each case relative to the mobile phase.

Even more preferably the mobile phase contains 7.5 vol. % to 17.5 vol. % organic solvent, relative to the mobile phase, and for this to be made up to 100 vol. % with the aqueous buffered solvent.

Elution may proceed isocratically or by means of gradient separation. In isocratic separation, elution of the RNA proceeds with a single eluent or a constant mixture of a plurality of eluents, wherein the solvents described above in detail may be used as eluent.

In a preferred embodiment, gradient separation is performed wherein the composition of the eluent is varied by means of a gradient program. The equipment necessary for gradient separation is known to a person skilled in the art. Gradient elution may here proceed either on the low pressure side by mixing chambers or on the high pressure side by further pumps.

Preferably, the proportion of organic solvent, as described above, is increased relative to the aqueous solvent during gradient separation. The above-described agents may here be used as the aqueous solvent and the likewise above-described agents may be used as the organic solvent. For example, the proportion of organic solvent in the mobile phase may be increased in the course of HPLC separation from 5.0 vol. % to 20.0 vol. %, in each case relative to the mobile phase. In particular, the proportion of organic solvent in the mobile phase may be increased in the course of HPLC separation from 7.5 vol. % to 17.5 vol. %, in particular 9.5 to 14.5 vol. %, in each case relative to the mobile phase.

The following gradient program has proven particularly favourable for the purification of RNA:
Eluent A: 0.1 M triethylammonium acetate, pH 7
Eluent B: 0.1 M triethylammonium acetate, pH 7, with 25 vol. % acetonitrile Eluent composition:
   start: 62% A and 38% B (1 st to 3rd minute)
   increase to 58% B (1.67% increase in B per minute), (3rd-15th minute)
   100% B (15th to 20th minute)

Another example of a gradient program is described below, the same eluent A and B being used:
Eluent Composition:
   starting level: 62% A and 38% B (1 st-3rd min)
   separation range I: gradient 38%-49.5% B (5.75% increase in B/min) (3rd-5th min)
   separation range II: gradient 49.5%-57% B (0.83% increase in B/min) (5th-14th min)
   rinsing range: 100% B (15th-20th min)

It is preferred to use purified solvent for HPLC. Such purified solvents are commercially obtainable. They may additionally also be filtered through a 1 to 5 μm microfilter, which is generally mounted in the system upstream of the pump. It is additionally preferred for all the solvents to be degassed prior to use, since otherwise gas bubbles occur in most pumps. If air bubbles occur in the solvent, they may interfere not only with separation but also with the continuous monitoring of outflow in the detector. The solvents may be degassed by heating, by vigorous stirring with a magnetic stirrer, by brief evacuation, by ultrasonication or by passing a small stream of helium through the solvent storage vessel.

The flow rate of the eluent is selected such that good separation of the RNA from the other constituents contained in the sample to be investigated takes place. The eluent flow rate may amount to from 1 ml/min to several liters per minute (in the case of upscaling), in particular about 1 to 1000 ml/min, more preferably 5 ml to 500 ml/min, even more preferably more than 100 ml/min, depending on the type and scope of the upscaling. This flow rate may be established and regulated by the pump.

The HPLC is preferably performed under denaturing conditions, such as an increased temperature. Suitable temperature conditions include a temperature of at least 70° C., preferably of at least 75° C., more preferably of about 78° C. By using denaturing conditions any intramolecular double strands formed between two RNA strands or between an RNA strand and a DNA strand are disrupted so that only single-stranded nucleic acid molecules are present in the sample.

Detection proceeds preferably with a UV detector at 254 nm, wherein a reference measurement may be made at 600 nm. However, any other detection method may alternatively be used, with which the RNA may be detected.

For preparative purification of the RNA, it is advisable to collect the RNA-containing eluted solvent quantities. In this respect, it is preferred to carry out this collection in such a way that the eluted solvent is collected in individual separated fractions. This may take place for example with a fraction collector. In this way, the high-purity RNA-containing fractions may be separated from other RNA-containing fractions which still contain undesired impurities, albeit in very small quantities. The individual fractions may be collected for example over 1 minute.

The HPLC is preferably performed under completely denaturing conditions. This may proceed for example in that sample application takes place at a temperature of 4-12° C., the HPLC method otherwise proceeding at a higher temperature, preferably at 70° C. or more, particularly preferably at 75° C. or more, in particular up to 82° C., and very particularly preferably at about 78° C.

Sample application may be performed with two methods, stop-flow injection or loop injection. For stop-flow injection a microsyringe is used which is able to withstand the high pressure applied in HPLC. The sample is injected through a septum in an inlet valve either directly onto the column packing or onto a small drop of inert material immediately over the packing. The system may in this case be under elevated pressure, or the pump may be turned off prior to injection, which is then performed when the pressure has fallen to close to the normal value. In the case of loop injection, a loop injector is used to introduce the sample. This consists of a tubular loop, into which the sample is inserted. By means of a suitable rotary valve, the stationary phase is then conveyed out of the pump through the loop, whose outlet leads directly into the column. The sample is entrained in this way by the stationary phase into the column, without solvent flow to the pump being interrupted.

In a particularly preferred embodiment, the material for the reversed phase is a poly-styrenedivinylbenzene, wherein in particular non-alkylated polystyrenedivinyl-benzene may be used. A non-alkylated porous polystyrenedivinylbenzene which is very particularly is one which has in particular a particle size of 8.0±1.5 µm, in particular 8.0±0.5 µm, and a pore size of 1000- or 4000 Å. With this material for the reversed phase, the advantages described below may be achieved in a particularly favourable manner.

The eluate of the RP-HPLC step contains the RNA. The RNA in the eluate is purified as compared to the RNA sample subjected to the RP-HPLC step.

After the RP-HPLC step any organic solvent present in the eluate may be removed by suitable methods which are known to the skilled person. These methods include, but are not limited to, precipitation with isopropanol or lithium chloride, tangential flow filtration and dialysis. In a preferred embodiment the organic solvent is removed by precipitation of the RNA with isopropanol.

The purified RNA which is obtained by the method of the present invention can be used to prepare a pharmaceutical composition. The pharmaceutical composition can be prepared by admixing the RNA with one or more pharmaceutically acceptable carriers. Sterile injectable forms of the pharmaceutical composition may be aqueous or oleaginous suspension. These suspensions may be formulated according to techniques known in the art using suitable dispersing or wetting agents and suspending agents. A pharmaceutically acceptable carrier typically includes the liquid or non-liquid basis of a composition comprising the components of the composition. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the pharmaceutical composition. The term "compatible" as used here means that these constituents of the inventive pharmaceutical composition are capable of being mixed with the components of the pharmaceutical composition in such a manner that no interaction occurs which would substantially reduce the pharmaceutical effectiveness of the pharmaceutical composition under typical use conditions.

Although the method of the present invention is particularly suitable for use in the context of small scale RNA purification, it may also be used with larger amounts of RNA such as several 100 grams of RNA. Preferably, the method of the present invention yields an amount of purified RNA of 0.1 g to 5 g, more preferably of 0.3 g to 3 g and most preferably of 0.5 g to 2 g. To obtain this amount of purified RNA 0.23 g to 11.6 g, preferably 0.69 g to 6.9 g and more preferably 1.16 g to 4.65 g of RNA have to be subjected to the method of the present invention.

The method with the method steps as defined herein may not only be used to purify RNA, but also to polish RNA preparations, i.e. to remove residual impurities from a partially purified RNA sample, to concentrate the RNA preparation and to re-buffer the RNA preparation and to capture RNA present in a solution.

The present invention was made with support from the Government under Agreement No. HR0011-11-3-0001 awarded by DARPA. The Government has certain rights in the invention.

EXAMPLES

The following Examples are merely illustrative and shall describe the present invention in a further way. The Examples shall not be construed to limit the present invention thereto.

Example 1: Preparation of RNA Solutions

1. Preparation of DNA and mRNA Constructs:

For the present Examples, a DNA sequence was prepared by modifying the DNA sequence by GC-optimization for stabilization. The GC-optimized DNA sequence was introduced into a pUC19 derived vector.

2. RNA In Vitro Transcription:

The obtained plasmid DNA was used for RNA in vitro transcription experiments to obtain the RNA according to SEQ ID NO: 1.

The EcoRI linearized DNA plasmid was transcribed in vitro using T7 polymerase. RNA in vitro transcription was performed in the presence of a CAP analog (m7GpppG). RNA in vitro transcription was carried out in 5.8 mM m7G(5')ppp(5')G Cap analog, 4 mM ATP, 4 mM CTP, 4 mM UTP, and 1.45 mM GTP, 50 µg/ml DNA plasmid, 80 mM HEPES, 24 mM MgCl$_2$, 2 mM Spermidine, 40 mM DTT, 100 U/µg DNA T7 RNA polymerase, 5 U/µg DNA pyrophosphatase, and 0.2 U/µl RNAse inhibitor. The in vitro transcription reaction was incubated for 4.5 hours at 37° C.

To remove DNA template, 0.66 mM CaCl$_2$ and 300 U/ml DNase1 (Thermo Fisher) was added and incubated in digestion buffer for 2 h at 37° C. The digestion reaction was stopped by adding EDTA to a final concentration of 25 mM. In the following examples the obtained preparation is referred to as "crude RNA IVT reaction".

Optionally, the crude RNA IVT reaction was HPLC purified using PureMessenger® (CureVac, Tubingen, Germany; according to WO 2008/077592 A1). HPLC-purified RNA eluates were precipitated using isopropanol precipitation in order to remove organic solvent. The samples were mixed with 5 M NaCl and 100% isopropanol. After incubation at 4° C., the reaction vials were centrifuged, and supernatants were discarded. The RNA pellets were washed with ethanol, centrifuged, and supernatant was removed. The obtained RNA pellets were dried for 30 minutes at room temperature and eventually re-suspended in 2 ml WFI.

In the following examples the purified RNA preparation is referred to as "HPLC purified RNA".

Example 2: Purification of HPLC Purified RNA Using Hydrophobic Interaction Chromatography (HIC)

1. Buffers and Basic Procedure:

1 ml HPLC purified RNA probe was mixed with 10 ml high salt binding buffer to obtain a diluted RNA solution (about 0.2 mg/ml). The CIM-OH column was attached to the FPLC device (ÄKTA avant) and equilibrated with 20 ml 50% high salt binding buffer. The maximal pressure was set to 5 MPa. The flow rate was 3 ml/min. After loading of 2.5 ml probe onto the CIM-OH column, the salt concentration was gradually reduced by adding low salt elution buffer. During the procedure, different fractions were taken. Moreover, the flow through was collected. Both, the collected fractions and flow through were analyzed (SDS page, Agarose gel electrophoresis).

2. HIC Using a CIM-OH Column (2 M NaCl in High Salt Binding Buffer):

HPLC purified RNA (R2025) was used as probe. To purify/concentrate HPLC-purified RNA, a CIM-OH column (CIM-OH, 340 µl CV, BIA separations) was attached to the FPLC device (ÄKTA avant, GE Healthcare Life Sciences) purged with ddH20 and equilibrated (equilibration buffer: 20 mM HEPES-NaOH, pH7.0; 2M NaCl). Then, 2 mg/ml RNA (R2025) was diluted 1:10 with equilibration buffer and 500 µg RNA was loaded onto the respective column with 2 ml min-1 and a maximum pressure of 5 MPa. The captured RNA was eluted using a gradually decreasing salt gradient with a flow rate of 3 ml min-1 (elution buffer: 20 mM HEPES-NaOH, pH 7.0). The elution profile of the RNA is shown in FIG. 1.

Shortly after subjecting the RNA sample to the CIM-OH column (1), unbound sample was eluted by washing with equilibration buffer (2) that potentially comprised contaminants (e.g. spermidine, proteins). While decreasing the salt concentration via increasing the concentration of the low salt buffer (elution buffer: 20 mM HEPES-NaOH, pH 7.0) (3) the RNA fraction eluted as a sharp and defined peak (4).

2. HIC Using CIM-SO3 Columns

Figure 2:
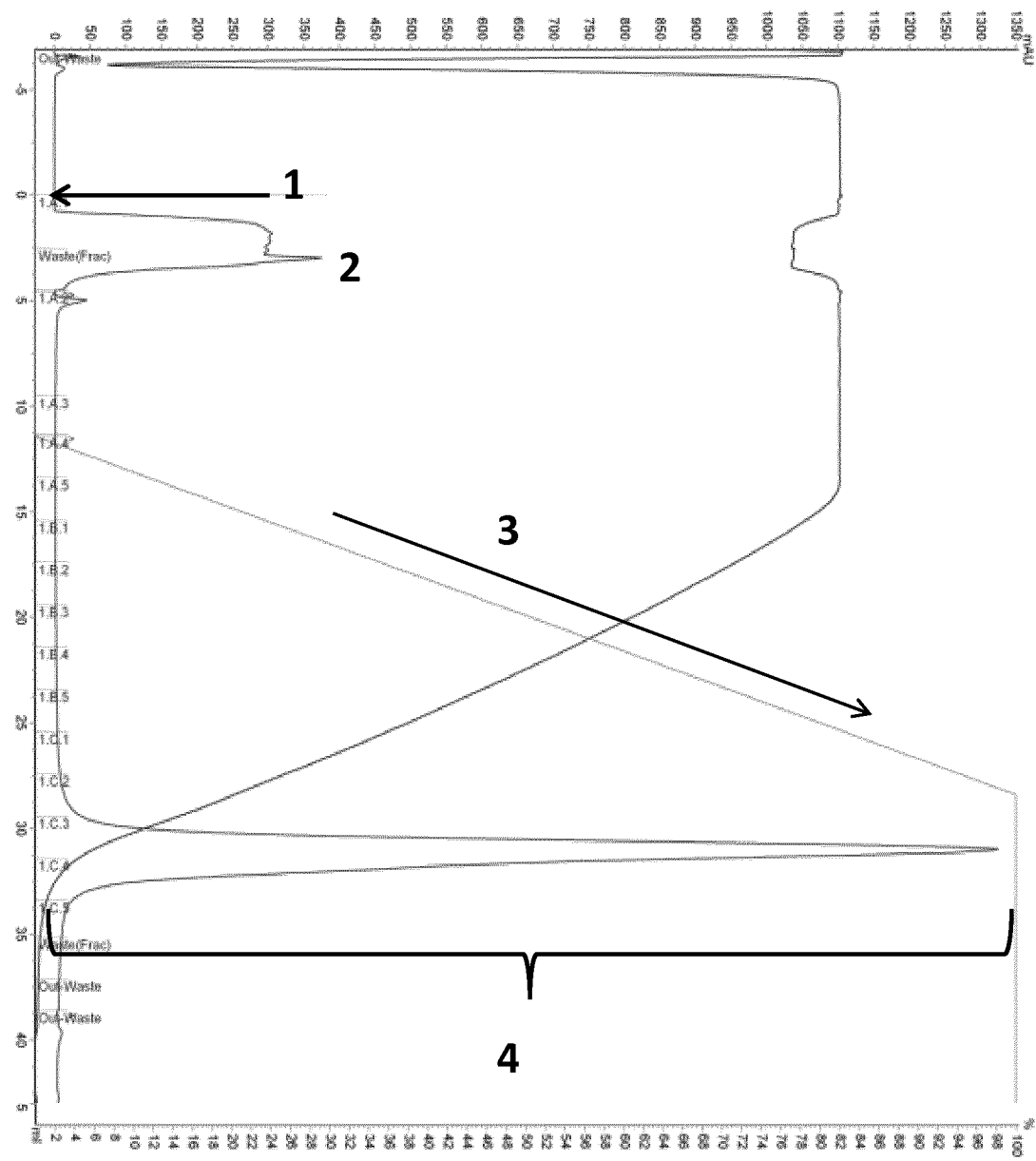

To purify/concentrate HPLC-purified RNA, a CIM-SO$_3$ column (CIM-SO$_3$, 340 µl CV, BIA separations) was attached to the FPLC device (ÄKTA avant, GE Healthcare Life Sciences) purged with ddH$_2$0 and equilibrated (equilibration buffer: 20 mM HEPES-NaOH, pH7.0; 2M NaCl). Then, 2 mg/ml RNA (R2025) was diluted 1:10 with equilibration buffer and 500 µg RNA was loaded onto the respective column with 2 ml min-1 and a maximum pressure of 5 MPa. The captured RNA was eluted using a gradually decreasing salt gradient with a flow rate of 3 ml min-1 (elution buffer: 20 mM HEPES-NaOH, pH 7.0). The elution profile of the RNA is shown in FIG. 2. Shortly after subjecting the RNA sample to the CIM-OH column (1), unbound sample was eluted by washing with equilibration buffer (2) that potentially comprised contaminants (e.g. spermidine, proteins). While decreasing the salt concentration via increasing the concentration of the low salt buffer (elution buffer: 20 mM HEPES-NaOH, pH 7.0) (3) the RNA fraction eluted as a sharp and defined peak (4).

Result:

Unexpectedly, the results show that HIC is a suitable method for capturing RNA from a HPLC purified RNA sample. Particularly suitable are monolithic column materials (CIM) bearing —OH and SO$_3$ moieties as they show high binding capacity for large RNA molecules. The results suggest that the inventive method may be broadly applicable for the purification and also for the re-buffering, conditioning, cleaning, polishing, concentrating and/or capturing of various kinds of RNA preparations. One further advantage of the used material (CIM monolith) is that said materials have a large working pH range (pH 2-pH13) allowing for cleaning-in place with e.g. alkaline cleaning solutions. Another advantage of the used material (CIM monolith) is that those macroporous monoliths also allow for large-scale preparations as these columns can be used with high flow rates.

To evaluate if the inventive method also works for crude RNA preparations containing multiple contaminations, the inventive HIC method was applied to purify crude RNA IVT samples (see Example 3).

Example 3: Purification of Non-Purified RNA from a Crude RNA IVT Reaction Using Hydrophobic Interaction Chromatography (HIC)

Figure 3:
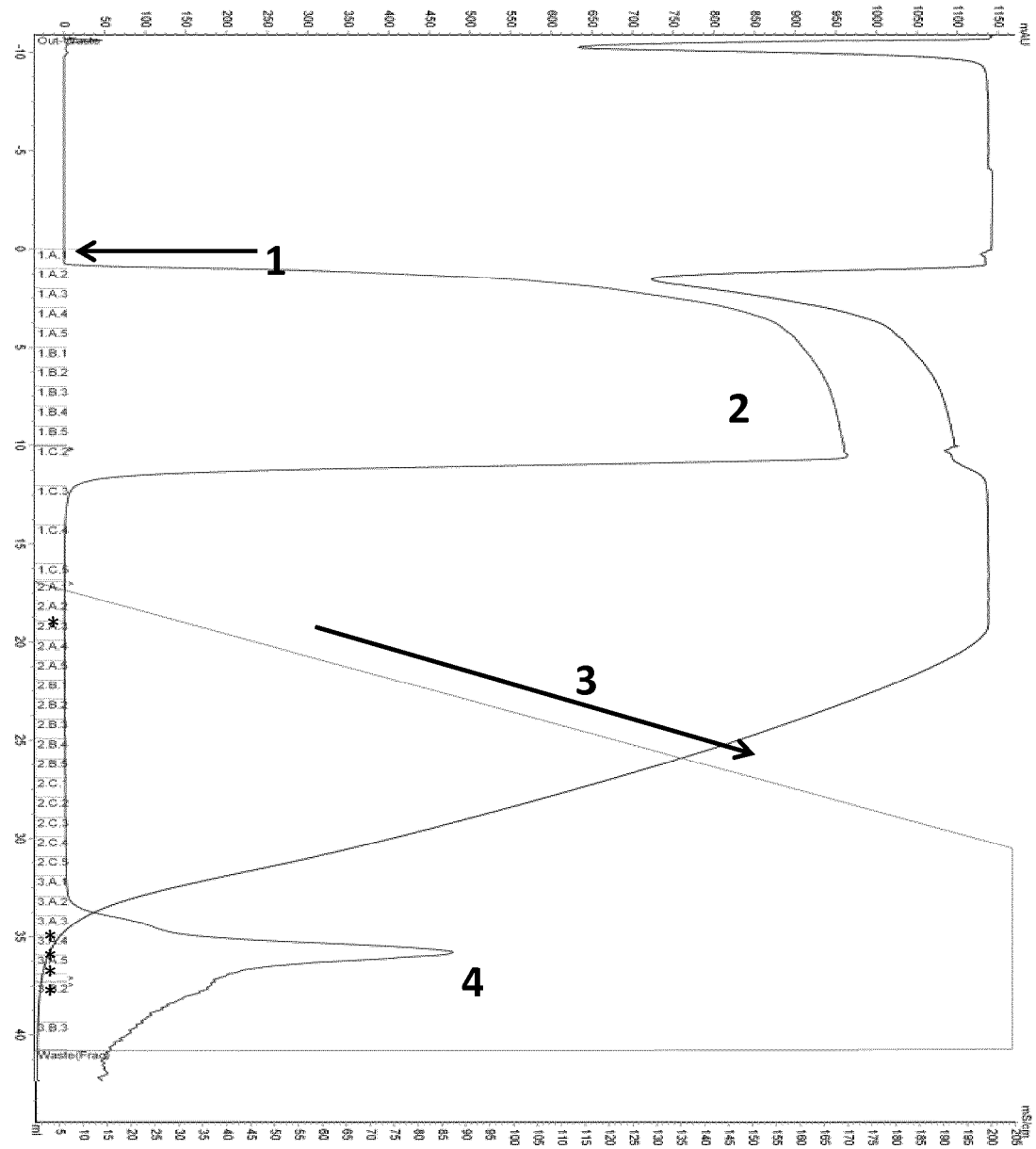

To test if also crude IVT RNA samples (prepared according to Example 1) could be purified using the inventive HIC method, 200 µl of a non-purified IVT RNA sample (1.3 mg/ml) was diluted 1:10 in equilibration buffer and applied to a monolithic CIM column (CIM-OH; 2 ml min$^{-1}$, maximum pressure of 5 MPa). Elution of the RNA was performed via increasing the concentration of the low salt elution buffer (elution buffer: 20 mM HEPES-NaOH, pH 7.0). Detection was performed via UV measurement at 260 nm. The elution profile of the RNA is shown in FIG. 3.

Figure 4:
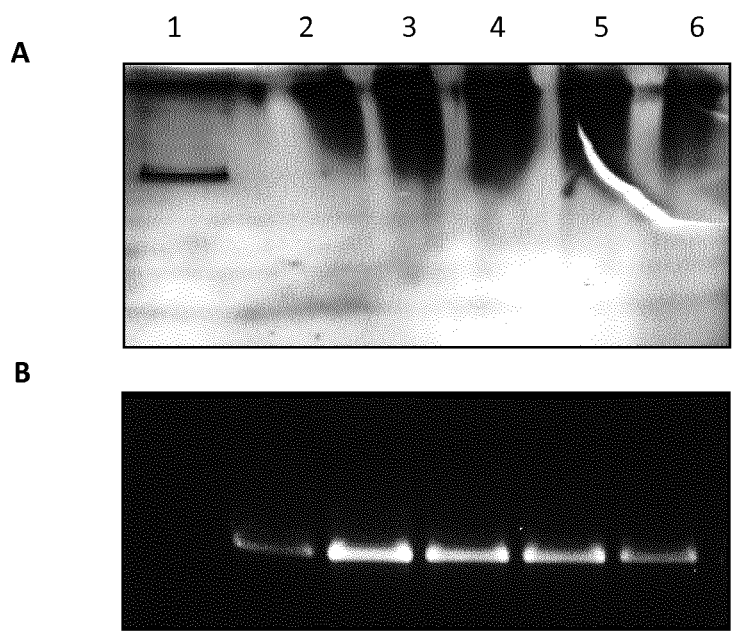

Shortly after subjecting the crude IVT RNA sample to the CIM-OH column (1), unbound flow through waste sample was eluted by washing with equilibration buffer (2) that comprised multiple protein contaminants (e.g. T7 RNA Polymerase, Pyrophosphatase, etc.) of the crude IVT RNA reaction. While decreasing the salt concentration via increasing the concentration of the low salt buffer (elution buffer: 20 mM HEPES-NaOH, pH 7.0) (3) the RNA fraction eluted as a sharp and defined peak (4). During elution, samples from the flow through and 5 different fractions after applying the elution buffer were taken. Although the very high A260 nm signal of the flow-through peak is indicative for salts and other low molecular weight components of the IVT mix (e.g. DTT and nucleotides), SDS-PAGE with subsequent silver staining was performed in order to detect proteins in single fractions (FIG. 4a). Whereas no proteins could be detected in elution fractions, protein contamination was found in the flow-through fraction. Agarose gel electrophoresis analysis of the fractions shows that RNA cannot be found in the flow through but accumulates after increase of elution buffer (FIG. 4b).

Result:

The results show that the inventive HIC method is suitable for capturing, purifying and re-buffering of an RNA sample containing multiple contaminations (crude IVT RNA sample). The results indicate that the method may be broadly applicable for the purification and also for the re-buffering, conditioning, cleaning, polishing, concentrating and/or capturing of RNA from various sources (e.g., crude RNA preparations, crude RP-HPLC reactions etc.).

FIGURE LEGENDS

FIG. 1:

Elution profiles of a HIC with a CIM-OH column of 0.5 µg HPLC purified RNA under decreasing salt concentrations. 1: RNA sample subjected to CIM-OH, 2: waste fraction, 3: gradual increase of elution buffer, 4: RNA fraction. A detailed description of the experiment is provided in the example section, Example 2.

FIG. 2:

Elution profiles of a HIC with a CIM-SO3 column using 0.5 µg purified RNA under decreasing salt concentrations. 1: RNA sample subjected to CIM-SO3; 2: waste fraction; 3: gradual increase of elution buffer; 4: RNA fraction. A detailed description of the experiment is provided in the example section, Example 2.

FIG. 3:

Elution profiles of a HIC with a CIM-OH column using 0.5 µg RNA under decreasing salt concentrations. 1: RNA sample subjected to CIM-OH; 2: waste fraction; 3: gradual increase of elution buffer; 4: RNA fraction. Asterisks indicate fractions that were further analyzed (see FIG. 4). A detailed description of the experiment is provided in the example section, Example 3.

FIG. 4:

(A) Analysis of flow-through (1) and five (2-6) elution fractions (as indicated in FIG. 3) via silver staining of SDS-PAGE (which stains proteins and nucleic acids). (B) Agarose gel electrophoresis of the same samples. A detailed description of the experiment is provided in the example section, Example 3.

The invention claimed is:

1. A method for purifying RNA, comprising the steps of:
   a) applying a sample containing in vitro transcribed RNA in an equilibration buffer having a high salt concentration to a support material that binds the RNA under said high salt concentration, wherein the support material comprises a binding ligand consisting of hydroxyl or sulfate groups and, wherein the equilibration buffer has said high salt concentration of at least about 150 mM;
   b) optionally washing the support material with a washing buffer having a high salt concentration of at least about 150 mM; and
   c) eluting the RNA from the support material with an elution solution.

2. The method according to claim 1, wherein the equilibration buffer and/or the washing buffer has a salt concentration of 500 mM to 3 M.

3. The method according to claim 1, wherein the equilibration buffer and/or the washing buffer comprises sodium chloride or ammonium sulfate.

4. The method according to claim 1, wherein the equilibration buffer and/or the washing buffer comprises at least about 2 M NaCl.

5. The method according to claim 4, wherein the equilibration buffer and/or the washing buffer comprises 20 mM HEPES-NaOH, pH 7.0, 2 M NaCl.

6. The method according to claim 1, wherein the equilibration buffer and the washing buffer have the same composition and the same pH.

7. The method according to claim 1, wherein the support material is a monolithic support material.

8. The method according to claim 1, wherein the support material is a methacrylate polymer.

9. The method according to claim 1, wherein the RNA is eluted by gradually decreasing the salt concentration of the elution solution.

10. The method according to claim 1, wherein the elution solution does not contain a salt.

11. The method according to claim 1, wherein the elution solution comprises 20 mM HEPES-NaOH, pH 7.0.

12. The method according to claim 1, wherein the method comprises the steps of:
    a) transcribing RNA from a template DNA in vitro;
    b) applying a sample containing the in vitro transcribed RNA in an equilibration buffer having a high salt concentration of at least about 150 mM to a support material capable of binding the RNA under high salt conditions, wherein the support material comprises a binding ligand consisting of hydroxyl or sulfate groups;
    c) washing the support material with a washing buffer having a high salt concentration of at least about 150 mM; and
    d) eluting the RNA from the support material with an elution solution.

13. The method according to claim 12, further comprising a step a1) of degrading the template DNA.

14. The method according to claim 13, wherein the template DNA is degraded by treatment with DNase.

15. The method according to claim 12, further comprising a step a2) of subjecting the in vitro transcribed RNA to a reverse phase-HPLC step.

16. The method according to claim 12, wherein said RNA is suitable for preparing a pharmaceutical composition.

17. The method according to claim 2, wherein the RNA is a mRNA.

18. A method for preparing a pharmaceutical composition comprising:
    a) transcribing RNA from a template DNA in vitro;
    b) applying a sample containing the in vitro transcribed RNA in an equilibration buffer having a high salt concentration of at least about 150 mM to a support material capable of binding the RNA under high salt conditions, wherein the support material comprises a binding ligand consisting of hydroxyl or sulfate groups;
    c) washing the support material with a washing buffer having a high salt concentration of at least about 150 mM; and
    d) eluting the washed RNA from the support material with an elution solution; and
    e) formulating the eluted RNA into a pharmaceutical composition.

19. The method according to claim 18, wherein the equilibration buffer and/or the washing buffer comprise about 500 mM to 3 M NaCl.

20. The method according to claim 17, wherein the binding ligand contains hydroxyl groups.

21. The method according to claim 17, wherein the binding ligand contains sulfate groups.

* * * * *